United States Patent [19]
Taylor et al.

[11] Patent Number: 5,324,259
[45] Date of Patent: Jun. 28, 1994

[54] INTRAVASCULAR CATHETER WITH MEANS TO SEAL GUIDEWIRE PORT

[75] Inventors: Kevin D. Taylor; Eric Williams, both of San Jose; Alan K. Schaer, Cupertino, all of Calif.

[73] Assignee: Advanced Cardiovascular Systems, Inc., Santa Clara, Calif.

[21] Appl. No.: 809,888

[22] Filed: Dec. 18, 1991

[51] Int. Cl.⁵ ............................................. A61M 29/00
[52] U.S. Cl. ..................................... 604/96; 604/167; 606/194
[58] Field of Search .................. 604/96, 97–103, 604/52, 53, 167, 256, 247; 606/192–197

[56] References Cited
U.S. PATENT DOCUMENTS

| | | | |
|---|---|---|---|
| 4,137,906 | 2/1979 | Akiyama et al. | 128/2 A |
| 4,606,347 | 8/1986 | Fogarty et al. | 128/344 |
| 4,616,653 | 10/1986 | Samson et al. | 128/344 |
| 4,638,805 | 1/1987 | Powell | 128/344 |
| 4,646,742 | 3/1987 | Packard et al. | 128/344 |
| 4,715,378 | 12/1987 | Pope, Jr. et al. | 128/344 |
| 4,793,350 | 12/1988 | Mar et al. | 128/344 |
| 4,811,737 | 3/1989 | Rydell | 128/344 |
| 4,813,934 | 3/1989 | Engelson et al. | 604/99 |
| 4,848,344 | 7/1989 | Sos et al. | 128/344 |
| 4,857,054 | 8/1989 | Helfer | 604/102 |
| 4,929,235 | 5/1990 | Merry et al. | |
| 4,932,959 | 6/1990 | Horzewski et al. | 606/194 |
| 4,960,412 | 10/1990 | Fink . | |
| 5,085,636 | 2/1992 | Burns | 604/99 |

Primary Examiner—John D. Yasko
Attorney, Agent, or Firm—Crosby, Heafey, Roach & May

[57] ABSTRACT

This invention is directed to an intraluminal catheter, such as a dilatation catheter for angioplasty procedures, having a inner lumen which is adapted to receive a guidewire therein and to deliver inflation liquid to an inflatable member and which is provided with sealing means to prevent the loss of inflation fluid through the guidewire port in the distal end of the catheter. The sealing means is actuated by inflation fluid under pressure which is introduced into the interior of the guidewire receiving inner lumen.

23 Claims, 4 Drawing Sheets

INTRAVASCULAR CATHETER WITH MEANS TO SEAL GUIDEWIRE PORT

BACKGROUND OF THE INVENTION

This invention generally relates to intravascular catheters, such as balloon dilatation catheters used in percutaneous transluminal coronary angioplasty (PTCA).

In classic PTCA procedures, a guiding catheter having a preshaped distal tip is percutaneously introduced into the cardiovascular system of a patient and advanced therein until the preshaped distal tip of the guiding catheter is disposed within the aorta adjacent the ostium of the desired coronary artery. The guiding catheter is twisted or torqued from the proximal end to turn the distal tip of the guiding catheter so that it can be guided into the desired coronary ostium. With over-the-wire systems, a guidewire and a balloon dilatation catheter are introduced into and advanced through the guiding catheter to the distal tip thereof, with the guidewire slidably disposed within an inner lumen of the dilatation catheter. The guidewire is first advanced out the distal tip of the guiding catheter, which is seated in the ostium of the patient's coronary artery, until the distal end of the guidewire crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the balloon is inflated to a predetermined size with radiopaque liquid at relatively high pressures (e.g., generally 4–12 atmospheres) to dilate the stenosed region of the diseased artery. One or more inflations may be necessary to effectively dilate the stenosis. Additional stenoses may be dilatated with the same catheter. When the dilatations are completed, the balloon is deflated so that the dilatation catheter can be removed from the dilated stenosis and blood flow will resume through the dilated artery.

Further details of guiding catheters, dilatation catheters, guidewires, and other devices for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,538,622 (Samson et al.); U.S. Pat. No. 4,554,929 (Samson et al.); U.S. Pat. No. 4,582,181 (Samson); U.S. Pat. No. 4,616,625 (Simpson); U.S. Pat. No. 4,638,805 (Powell); U.S. Pat. No. 4,478,986 (Morrison et al.); U.S. Pat. No. 4,898,577 (Badger et al.); and U.S. Pat. No. 4,827,941 (Taylor et al.) which are hereby incorporated herein in their entirety by reference thereto.

Fixed-wire dilatation catheters for coronary angioplasty, which were first described in U.S. Pat. No. 4,252,181 (Samson), now U.S. Pat. No. Re. 33,166, are similarly used except there is no longitudinal movement between the guidewire and the catheter. The fixed-wire dilatation catheters generally have an outer tubular member with an inflatable balloon on the distal section thereof which is capable of dilating a stenosis, and a guiding member extending out through the distal end of the balloon which aids in advancing the catheter to a desired location within the patient's vasculature. They usually have no inner tubular member and therefore have lower profiles, e.g., transverse dimensions, than over-the-wire dilatation catheters having the same inflated balloon size. Moreover, because the fixed-wire catheters have the guidewire or guiding member fixed or at least restricted as to longitudinal movement, these catheters generally have greater pushability than over-the-wire type catheters such as described and claimed in U.S. Pat. No. 4,323,071 (Simpson-Robert). The lower profile and greater pushability of the fixed-wire dilatation catheters allows them to cross tighter lesions and to be advanced much deeper into a patient's coronary anatomy than the over-the-wire dilatation catheters of comparable sizes.

The assignee of the present invention, Advanced Cardiovascular Systems, Inc., markets an improved dilatation catheter under the trademark ACS RX (R) which is described and claimed in U.S. Pat. No. 5,040,548 (Yock), U.S. Pat. No. 5,061,273 (Yock) and U.S. Pat. No. 4,748,982 (Horzewski et al.). This dilatation catheter has a short guidewire receiving sleeve or inner lumen extending through a distal portion of the catheter. The sleeve or inner lumen extends proximally a distance of at least about 10 cm and usually not more than about 50 cm from a first guidewire port in the distal end of the catheter to a second guidewire port in the catheter spaced proximally from the inflatable member of the catheter. Preferably, a slit is provided in the wall of the catheter body which extends distally from the second guidewire port, preferably to a location proximal to the proximal end of the inflatable balloon. The structure of the catheter allows for the rapid exchange of the catheter without the need for an exchange wire or adding a guidewire extension to the proximal end of the guidewire. The design of this catheter has been widely praised by the medical profession and has been met with much success in the market place because of the advantages of its unique design.

A major and continual thrust of development work in the field of intravascular catheters, particularly coronary angioplasty catheters, has been to reduce the profile, i.e., transverse dimensions, of such catheters and to improve the flexibility thereof without detrimentally affecting the pushability, particularly in the distal portion of such catheters. A reduction in profile with little or no loss in pushability allow a dilatation catheter to be advanced much further into a patient's coronary vasculature and to cross much tighter lesions. Fixed-wire dilatation catheters have provided lower profiles and increased pushability, but their use in coronary angioplasty has recently been somewhat limited due to the fact that if the fixed-wire catheter must be removed from an arterial location, access to that location is usually lost. One of the advantages of the over-the-wire dilatation catheter systems over the fixed-wire systems is that the over-the-wire systems allow the guidewire to be left in place while the dilatation catheter is removed and replaced so as to not loose the arterial location.

What has been needed and heretofore unavailable is a low profile dilatation catheter which allows for catheter exchange without loss of arterial position, particularly such a catheter with a single inner lumen. The present invention satisfies this and other needs.

SUMMARY OF THE INVENTION

This invention is directed to an intravascular catheter which has the low-profile features of a fixed-wire catheter but which provides for guidewire movement and allows for catheter exchange while maintaining access to vascular location.

The catheter of the invention generally includes an elongated catheter body having an inner lumen which extends therein and means disposed in the inner lumen which is adapted to sealingly engage a guidewire or other guiding member disposed within the inner lumen when fluid under pressure is introduced into the inner lumen. A presently preferred means to sealingly engage the guidewire or guiding member is a tubular element having a section at one end which is secured within the inner lumen and a tapered section at the other end which is adapted to collapse against the guidewire or guiding member upon the introduction of fluid under significant pressure, e.g., more than one atmosphere, into the interior of the inner lumen. The tubular sealing means may be secured within the inner lumen in the distal portion of the catheter body with a large diameter section of the tubular sealing means bonded to the distal portion of the catheter body and with the tapered section extending proximally within the inner lumen. A similar sealing means may also be provided at a proximal portion of the catheter or within the adapter on the proximal end thereof to seal this portion of end of the catheter in a similar fashion. The tapered section of the sealing tubular member in these instances would extend distally. The sealing means eliminates the need for an inner tubular member found in over the wire systems and thereby provides a substantially reduced profile yet the catheter can be exchanged and the guidewire exchanged as in over-the-wire dilatation catheter systems.

In one presently preferred embodiment, a means is provided to support the inflatable member in the deflated condition. Suitable means for such purpose include a helical coil or tubular member extending through the interior of the inflatable member, e.g., a balloon, with spacing between the individual turns of the coil or apertures in the tubular member for the passage of inflation fluid between the inner lumen of the catheter body and the interior of the inflatable member.

The use of the dilatation catheter of the present invention in a coronary angioplasty procedure is much like the use of an over-the-wire type dilatation catheter wherein the guidewire is loaded into the inner lumen of the dilatation catheter and then the dilatation catheter-guidewire assembly is introduced into a previously positioned guiding catheter and advanced therein until the distal end of the assembly reaches the distal end of the guiding catheter which is seated in the ostium of the patient's coronary artery. The guidewire is first advanced out of the distal end of the guiding catheter into the coronary anatomy until the guidewire extends distally beyond a lesion to be dilated. The distal tip of the guidewire is usually shaped (curved) in a conventional fashion to enable the guidewire to be steered into side branches of the coronary artery while it is being advanced therein. The dilatation catheter is then advanced over the previously positioned guidewire until the inflatable member on the dilatation catheter extends across the stenotic region of the patient's artery. During the delivery of the catheter to the site of the lesion, the guidewire is freely slidable within the inner lumen of the catheter, but upon the introduction of inflation fluid under significant pressure into the inner lumen of the catheter body and the interior of the inflatable member to inflate the latter, the fluid pressure acts to press the small diameter end of a tapered tubular sealing means against the exterior of the guidewire so as to prevent the escape of inflation fluid out the distal end of the catheter body. Upon the deflation of the inflatable member at the completion of the dilatation, the fluid pressure decreases, releasing pressure against the tapered end of the sealing means against the exterior of the guidewire, allowing the guidewire to be moved more easily within the inner lumen of the catheter shaft.

The same tubular sealing means described above can also be employed with dilatation catheters adapted to be readily exchanged during the angioplasty procedure. As previously described, these catheters have a relatively short guidewire receiving inner lumen extending within the distal portion of the catheter with proximal and distal guidewire ports in fluid communication with the short inner lumen, where the proximal port is at least 10 cm from the distal guidewire port and a substantial distance from the proximal end of the catheter. In this embodiment, the short distal inner lumen may be port of the inflation lumen which extends through the catheter body but one tubular sealing member is secured at the proximal guidewire port with the tapered portion extending distally and another is secured at the distal guidewire port with the tapered portion extending proximally. When inflation fluid is introduced under significant pressure to inflate the balloon or other inflatable member on the catheter, the tapered portions of the tubular sealing elements at both the distal and proximal guidewire ports are sealingly engaged against the exterior of a guidewire disposed within the dilatation catheter and thereby prevent loss of inflation fluid through either of the guidewire ports.

The sealing members of the present invention provide a substantial improvement with catheters having a single inner lumen for both inflation and other fluids and guidewire movement which reduces considerably the transverse profile of the catheter. However, they can be employed in any catheter lumen which is subject to fluid under significant pressure.

These and other advantages of the invention will become more apparent from the following detailed description of the invention, when taken in conjunction with the accompanying exemplary drawings.

DETAILED DESCRIPTION OF THE INVENTION

Figure 1:
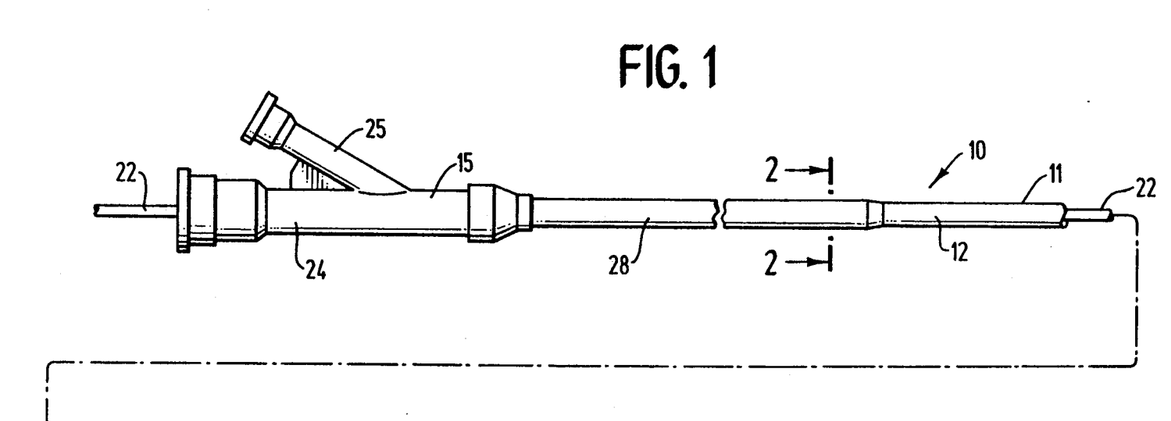
FIG. 1 is a longitudinal view, partially in cross-section of a dilatation catheter with a movable guidewire which embodies features of the invention.
Figure 2:
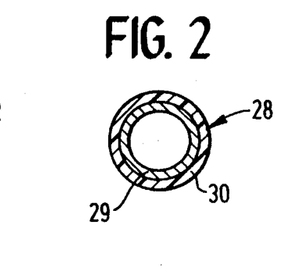
FIG. 2 is a transverse cross-sectional view of the catheter shown in FIG. 1 taken along the lines 2—2.

FIGS. 1 and 2 depict a dilatation catheter 10 which embodies features of the invention. As shown in the drawing, the catheter 10 generally includes an elongated catheter body 11 having a catheter shaft 12, a balloon 13 and a supporting helical coil 14 and an adapter 15 on the proximal end of the catheter body 11. A tubular sealing element 16 is disposed in the distal end of the catheter body and is preferably bonded by its distal extremity 17 in a suitable manner to the inside of the distal end 18 of the balloon 13.

The proximal extremity 20 of the sealing element 16 tapers inwardly in the proximal direction and is relatively flexible. When the inner lumen 21 which extends through the catheter shaft 12 and the interior of the balloon 13 are filled with inflation fluid under pressure, the proximal extremity 20 of the sealing element 16 is pressed against the exterior of the core member of guidewire 22 disposed within the inner lumen 21 by the pressurized fluid and thereby prevents the escape of significant quantities of inflation fluid through the distal guidewire port 23 in the distal end of the catheter body 11.

The proximal section 28 of the catheter shaft 12 is constructed of a hypotube 29 which may be covered with a polymer jacket or coating 30 of suitable material such as polyethylene. The distal section 31 of the catheter shaft is much shorter than the proximal section 28 and may be formed of a suitable polymer material such as a mixture of high density and low density polyethylene. The helical coil 14 may be formed of suitable metal or plastic materials, but preferably it is formed of a highly radiopaque material such as tungsten, platinum and alloys thereof which can provide high strength as well as a high degree of radiopacity which facilitates the fluoroscopic location of the balloon during an intravascular procedure. The balloon 13 may be formed of a variety of conventional relatively inelastic materials such as polyethylene, polyvinyl chloride, polyethylene terephthalate, ionomers such as Suryln ®, a registered trademark of E. I. DuPont Co., polyamide such a Nylon, and other suitable materials. The sealing element 16 may be formed of polyethylene of various densities, polyvinyl chloride, Nylon, composite materials and other suitable materials, which are well known to those skilled in the art. The dilatation balloon described in copending application Ser. No. 07/758,630, filed Sep. 12, 1991, which is incorporated herein in its entirety by reference, may also be employed. The other components of the dilatation catheter may be made of conventional materials. The junctions between catheter components can be heat seal junctions or they can be made with suitable adhesives such as various cyanoacrylate and U.V. curable adhesives sold under the trademark Loctite ®.

The size of the various components will depend upon the end use contemplated. For coronary angioplasty the overall length of the dilatation catheter is typically about 150 cm. Typical dimensions for the various components for a coronary dilatation catheter adapted for use with a guidewire having an outer diameter of 0.01 inch (0.254 mm) are set out in the table below:

| COMPONENT | I.D. | O.D. | LENGTH |
|---|---|---|---|
| Proximal Hypotube | 0.023 in | 0.028 in | 100 cm |
| Hypotube Jacket | 0.028 in | 0.032 in | 108 cm |
| Distal Shaft | 0.018 in | 0.025 in | 35 cm |
| Support Coil | 0.014 in | 0.023 in | 3 cm |
| Sealing Member | 0.018/ 0.011 in | 0.023/ 0.014 in | 6 mm |
| Tapered Distal Tip | 0.012 in | 0.025 in | 5 mm |

Unmentioned dimensions are generally conventional. Catheters designed for use with other sized guidewires will have correspondingly different dimensions.

Figure 3:
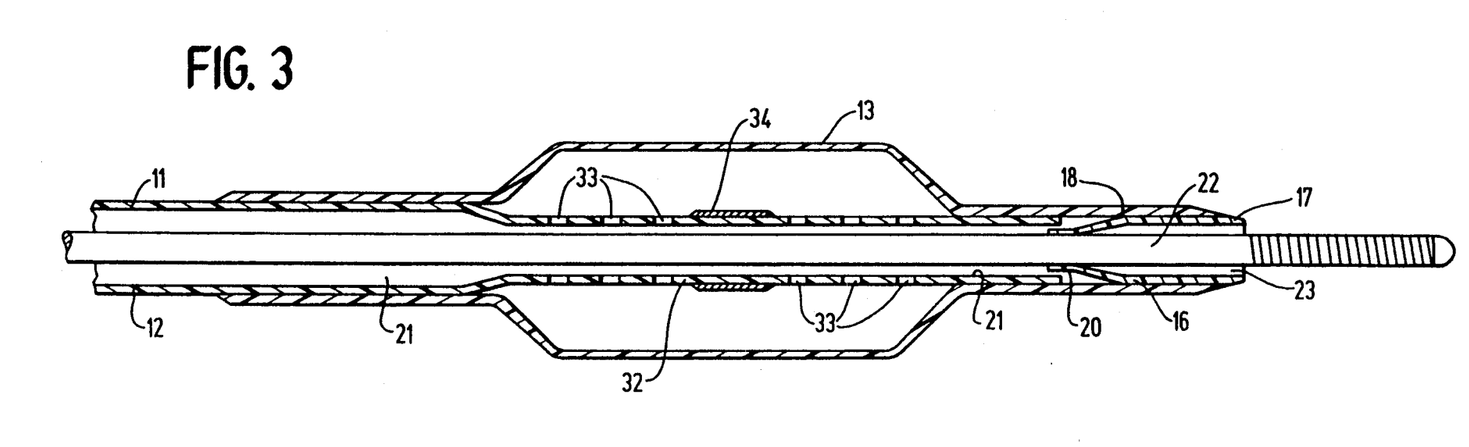
FIG. 3 is a partial longitudinal view in section of an alternative embodiment of the invention wherein a tubular support member with apertures within the wall thereof to direct inflation fluid into the interior of the inflatable member.

FIG. 3 illustrates an alternative embodiment of the invention wherein the distal shaft 12 is provided with a tubular extension 32 which extends through the interior of balloon 13 and supports the balloon in the deflated condition. The extension 32 also transmits pushing forces to the distal tip of the catheter body 11. Apertures 33 are provided in the wall of the tubular extension 32 to direct inflation fluid from the inner lumen 21 into the interior of balloon 13. A radiopaque marker 34 is provided on the exterior of extension 32 at the center of the balloon 13 to facilitate the fluoroscopic observation of the balloon within a patient. The rest of this alternative embodiment is essentially the same as that shown in FIGS. 1 and 2 with corresponding components being numbered the same.

Figure 4:
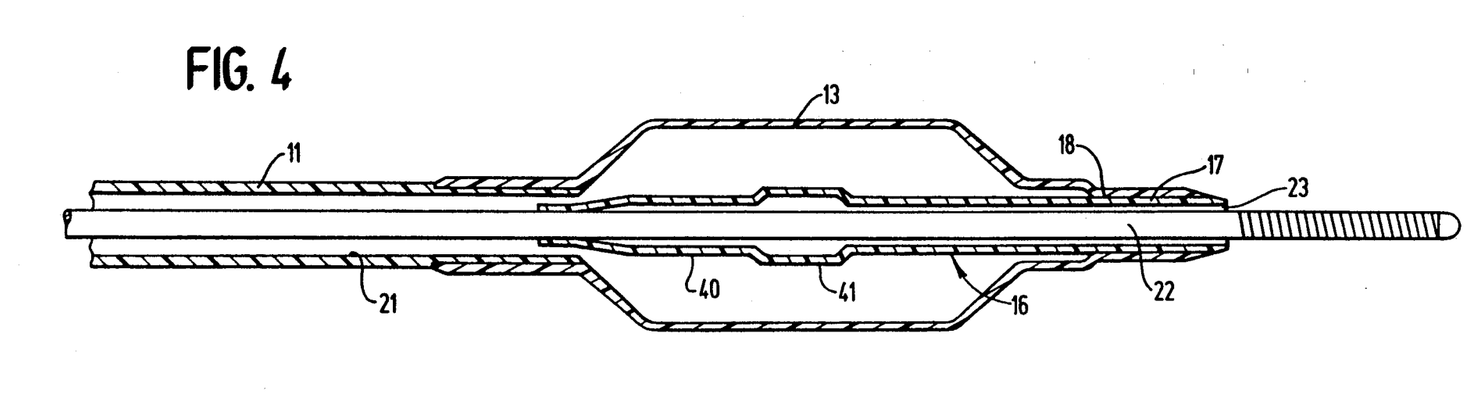
FIG. 4 is a partial longitudinal view in section of an additional alternative embodiment of the invention having the means to seal the guidewire is an elongated tubular element which has its distal end secured to the distal end of the balloon and which extends proximally across the interior of the inflatable member.

Another alternative embodiment of the invention is shown in FIG. 4 wherein the sealing member 16 is an elongated tubular member 40 which extends within the interior of the balloon 13. The tubular member 40 has a small expanded section 41 which is adapted to more readily collapse onto the guidewire 21 upon the introduction of inflation fluid under pressure to ensure a minimal blockage of inflation fluid out the guidewire port 23 in the distal end of the catheter shaft 11. Except as noted above this embodiment is essentially the same as the previously discussed embodiments. The corresponding components are numbered the same.

Figure 5:
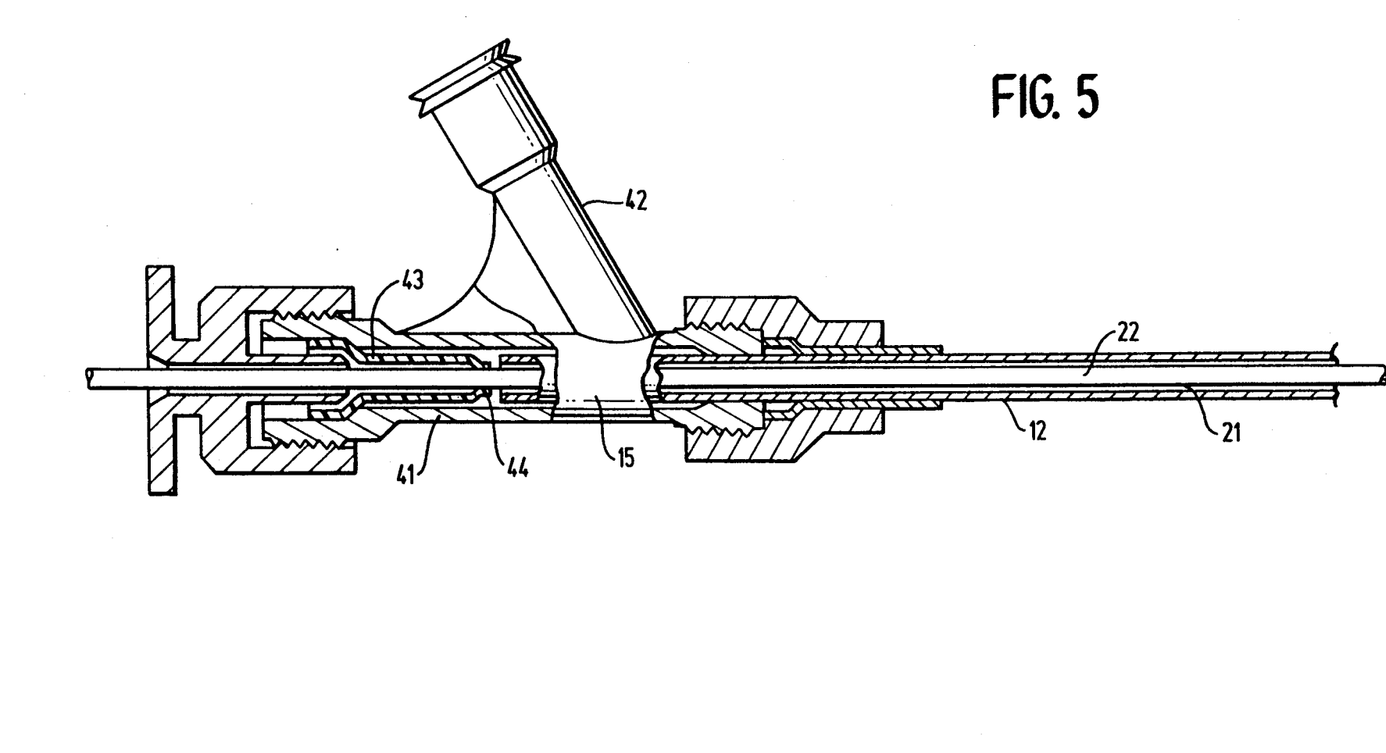
FIG. 5 is an elevational view, partially in section, of an adapter on the proximal end of the catheter shaft having embodiments of the invention.

As best shown in FIG. 5, the adapter 15 mounted on the proximal end of the catheter shaft 12 has two arms, a central arm 41 through which the proximal end of the guidewire 21 extends and a side arm 42 which is adapted to direct inflation fluid under pressure from a source not shown through the inner lumen 22 which extends through the catheter shaft 12 to the interior of the balloon 13. A tubular sealing element 43 is provided in central arm 41 with a tapered distal extremity 44 which is adapted to be sealingly pressed against the exterior of the core member of a guidewire 21 disposed therein upon the introduction of inflation fluid through the side arm 42. The proximal end of the tubular sealing element 43 is bonded by suitable means, e.g. a cyanoacrylate adhesive, to the interior or the central arm as shown. The tubular sealing element 43 operates in the same fashion as tubular element 16 with the tapered section thereof pressing against the exterior of the guidewire 21 so as to prevent the bypass of liquid to the exterior of the adapter 15.

The dilatation catheter of the invention can be used in a conventional over-the-wire fashion in a wide variety of intraluminal procedures, including coronary angioplasty. Depending upon the nature of the plaque which forms the stenosis, the fluid pressure required within the inflatable member for effective dilatation of the stenosis, can range from about 4 to about 20 atmospheres. However, notwithstanding the pressure used to dilate the stenosis, the sealing means prevents the loss of fluid through the guidewire ports. Upon deflating the balloon, the pressure of the sealing means against the exterior of the guidewire or other guiding member is released. In catheter systems where the guidewire or guiding member is not fixed, it may then be moved.

Usually, the inflatable member is maintained in the inflated condition for less than one minute to avoid generating ischemic conditions in tissue distal to the stenosis site. More than one inflation may be required to effectively dilatate the stenosis, and several stenoses may be dilated with the same catheter. Upon completion of the one or more dilations, the balloon is deflated and the catheter withdrawn from the patient. The guidewire may also be withdrawn form the patient at that time, but frequently the guidewire is left in the patient so as to ensure access to the stenotic site in case reaccessing the stenotic region is necessary due to an occlusion, an arterial spasm or the like.

FIGS. 6-10 illustrate an embodiment of the invention incorporated within another type of dilatation catheter which is designed for ready exchangeability such as described in U.S. Pat. No. 4,748,982, U.S. Pat. No. 5,040,548 and U.S. Pat. No. 5,061,273 which have been incorporated by reference herein. The catheter 50 generally includes an elongated catheter body 51 with an inner lumen 52 and an inflatable balloon 53 on the distal extremity thereof. The catheter body 51 includes a main shaft 54 and a shorter and more flexible secondary shaft 55 secured by its proximal end to the distal end of the main shaft in the transition region 56 which itself may be a separate member interconnecting the main and secondary shafts. A tubular sealing member 57 with tapered proximal extremity 58 is disposed within the distal portion of the secondary shaft 55 as shown. The transition region 56 has disposed therein a sealing tubular member 59 with a tapered distal section 60. The sealing member 59 is essentially the same as sealing member 57 except that its orientation is in the opposite direction. In some instances it may be desirable to provide an expanded spring coil (not shown) which extends distally from the tapered section 60 of the sealing element 59 to a narrowed portion of the secondary shaft 55 in order to guide guidewire 61 to the sealing member 59 and out the proximal guidewire port 62. The guidewire port 62 is spaced at least about 10 cm and generally not more than about 50 cm from the distal guidewire port 63 in the distal end of the catheter 50. In this embodiment a tubular extension 64 of the secondary shaft 55 extends through the interior of balloon 53 providing support to the balloon in the inflated condition and the distal end of the balloon is secured to the distal end of the tubular extension 64 by a suitable means such as an adhesive. A radiopaque marker 65 of a coil of suitable material such as gold or platinum is mounted on the exterior of the tubular extension 64 to facilitate the fluoroscopic location of the balloon within a patient's blood vessel during the intravascular procedure.

Figure 6:
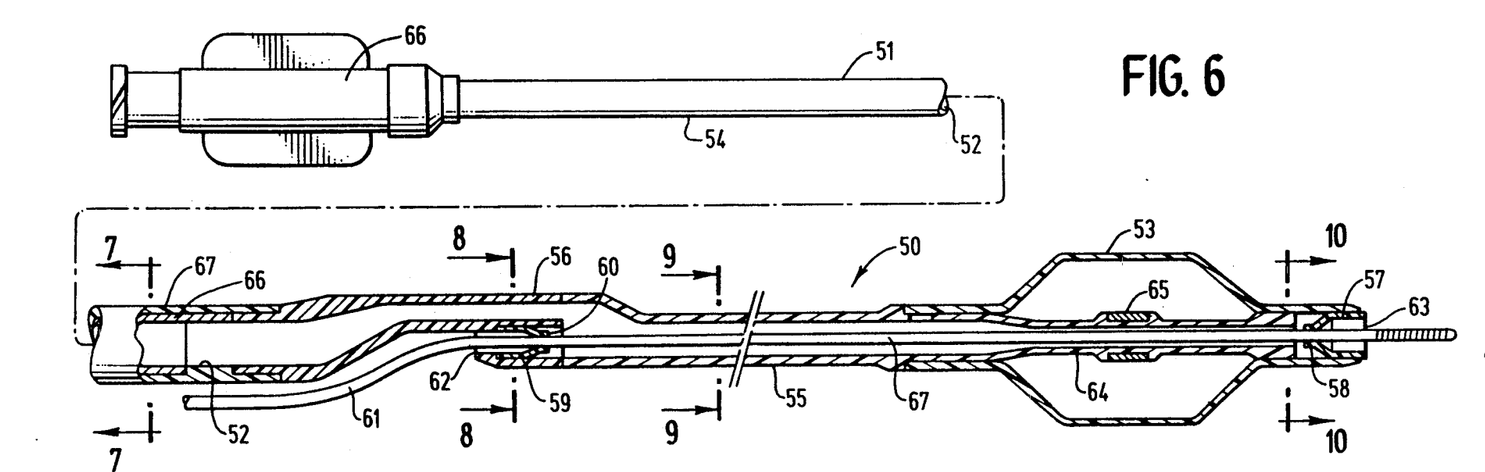
FIG. 6 is a longitudinal cross sectional view of another embodiment of the invention in a readily exchangeable dilatation catheter.

Upon the introduction of inflation liquid under pressure through the adapter 66 on the proximal end of the catheter 50 to inflate the balloon 53, the tapered extremities 58 and 60 of the sealing members 57 and 59 are pressed against the core member 67 of the guidewire 61 to thereby seal the proximal guidewire port 62 and the distal guidewire port 63 so as to prevent loss of inflation liquid therethrough.

The catheter shown in FIGS. 6-10 can be used in a conventional fashion whereby the guidewire 61 is first introduced into the inner lumen 52 and then both the guidewire and catheter are advanced through a guiding catheter previously positioned within the patient's vasculature. The catheter can also be use in the conventional method commonly called the "bare wire" technique. In this technique, the guidewire is previously disposed within the patient's coronary anatomy and the proximal end of the guidewire, which extends out of the patient, is mounted into the catheter 50 by inserting the proximal end of the guidewire 61 through the distal guidewire port 63 and and advancing it therein until it extends out the proximal guidewire port 62. The mounted catheter 50 may then be advanced over the guidewire to the desired location within the patient's vasculature. The catheter can be exchanged in the manner described in U.S. Pat. No. 4,748,982, U.S. Pat. No. 5,040,548 and U.S. Pat. No. 5,061,273 which have been incorporated herein.

Figure 7:
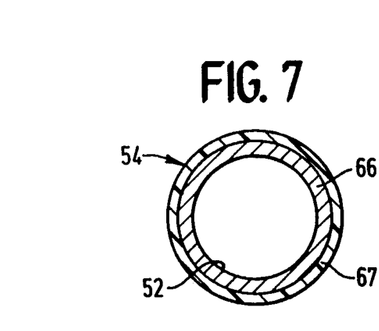
FIG. 7 is transverse cross-sectional view taken along the lines 7—7 shown in FIG. 6.
Figure 8:
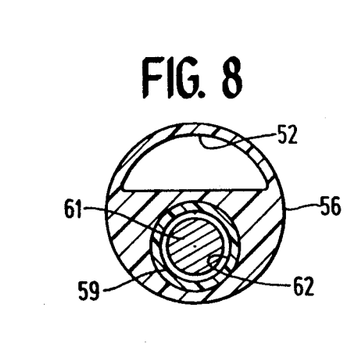
FIG. 8 is a transverse cross-sectional view taken along the lines 8—8 shown in FIG. 6.
Figure 9:
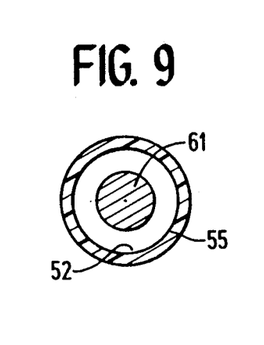
FIG. 9 is a transverse cross-sectional view taken along the lines 9—9 shown in FIG. 6.
Figure 10:
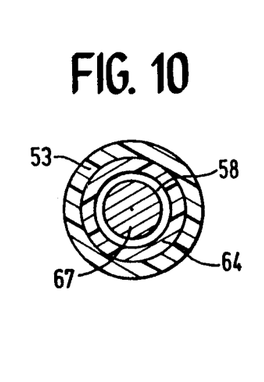
FIG. 10 is a transverse cross-sectional view taken along the lines 10—10 shown in FIG. 6.

As shown more clearly in FIG. 7, the main shaft 54 is preferably formed of hypotubing 68 and an outer plastic jacket or coating 69. The secondary shaft 55 and the transition region 56 are preferably formed of a mixture of high density and low density polyethylene. The transition region 56 may be heat formed in the desired shape to accommodate the tubular sealing member 59 and be adapted to join together the ends of the main shaft 54 and the secondary shaft 55.

While the invention has been described herein primarily in terms of a flexible tubular element which collapses against the exterior of a guidewire upon the introduction of inflation fluid under pressure into the inner lumen and the interior of the inflatable member, modifications can be made to the invention. For example, the sealing means can be a body of hydrophilic material disposed about the guidewire in the distal end of the catheter shaft 13 which expands upon contact with water-based inflation fluid when the fluid is introduced into the inner lumen of the catheter and interior of the inflatable member, such as described in copending application Ser. No. 07/631,657, filed Dec. 21, 1990 entitled "Fixed Wire Catheter With Rotatable Balloon Assembly", which is incorporated by reference herein in its entirety. The construction of the catheter incorporating this modification is essentially the same as the previously discussed embodiments except that the body of hydrophilic material surrounds the guidewire disposed within the distal end of the catheter body as disclosed in the above referenced co-pending application. However, in this instance there is no means to prevent movement of the guidewire before the inflation fluid is introduced under pressure into the catheter. Preferably, even with the expansion of the hydrophilic material to seal the guidewire so as to prevent the loss of liquid thereby, the guidewire would still be free to rotate or to move longitudinally.

Other modifications and improvements can be made to the invention without departing from the scope thereof.

What is claimed is:

1. An intraluminal catheter comprising:
  a) an elongated catheter body having proximal and distal ends with an inner lumen extending therein in fluid communication with a guidewire port in the distal end of the catheter body and adapted to receive an elongated guiding member;
  b) an inflatable member on the distal extremity of the elongated catheter body having an interior in fluid communication with the inner lumen of the elongated catheter body;

c) means disposed within a distal portion of the catheter body which is adapted to sealingly engage an elongated guidewire disposed therein when fluid under significant pressure is introduced into the inner lumen of the catheter; and d) an adapter mounted on the proximal end of the catheter body having an arm adapted to direct the guidewire into the inner lumen of the catheter body and having means to sealingly engage the guidewire extending through the adapter when fluid under significant pressure is introduced into the adapter.

2. The intraluminal catheter of claim 1 wherein at least one of the means to sealingly engage a guidewire is a tubular member with one end portion thereof secured within the inner lumen or the adapter and the other end portion thereof adapted to sealingly engage the exterior of the guidewire.

3. The intraluminal catheter of claim 2 wherein the sealing end portion of the tubular sealing means is tapered and is adapted to collapse to sealingly engage a guidewire disposed within the inner lumen upon the introduction of the fluid under pressure.

4. The intraluminal catheter of claim 1 wherein the means to sealingly engage a guidewire is secured within an adapter on the proximal end of the catheter body.

5. The intraluminal catheter of claim 1 wherein the means to sealingly engage a guidewire is secured within the catheter body proximal to the inflatable member.

6. The intraluminal catheter of claim 1 wherein the inflatable member is a balloon formed of relatively inelastic material.

7. The intraluminal catheter of claim 1 wherein the sealing means is an elongated tubular element which is secured by the distal extremity thereof to the distal end of the catheter body and the proximal extremity thereof extends well into the interior of the inflatable member.

8. The intraluminal catheter of claim 7 wherein the elongated tubular element which forms the sealing means has an expanded section which collapses against the guidewire and provides sealing effects to prevent the discharge of inflation fluid.

9. The intraluminal catheter of claim 1 wherein the sealing means is a body of hydrophilic material which swells about the guidewire upon contact with aqueous based inflation fluid.

10. The intraluminal catheter of claim 1 wherein the catheter body is provided with a proximal guidewire port spaced at least about 10 cm from the distal guidewire port, both the proximal and the distal guidewire ports being in fluid communication with the portion of the inner lumen extending therebetween within the catheter body.

11. The intraluminal catheter of claim 10 wherein a sealing means in provided in the inner lumen adjacent the proximal guidewire port which upon the introduction of inflation liquid into the inner lumen under significant pressure seals against the exterior of a guidewire disposed within the inner lumen and extending out the proximal guidewire port.

12. The intraluminal catheter of claim 1 wherein the catheter body has a single lumen extending essentially the length thereof which is adapted to receive a guidewire and to direct inflation fluid to the inflatable member.

13. A dilatation catheter for performing an angioplasty procedure, comprising:

a) an elongated catheter body having proximal and distal ends with an inner lumen extending therein which is in fluid communication with a guidewire port in the distal end of the catheter body and which is adapted to receive an elongated guidewire;

b) an inflatable member on a distal portion of the elongated catheter body having an interior in fluid communication with the inner lumen of the elongated catheter body;

c) means disposed within the distal portion of the catheter body which is adapted to sealingly engage an elongated guidewire disposed therein when inflation fluid under significant pressure is introduced into the inner lumen of the catheter to inflate the inflatable member; and d) an adapter on the proximal end of the catheter body having an arm adapted to direct the guidewire into the inner lumen of the catheter body and having means actuated by fluid to sealingly engage the guidewire extending through the adapter when fluid under significant pressure is introduced into the adapter.

14. The dilation catheter of claim 13 wherein the catheter body is provided with a proximal guidewire port in fluid communication with the inner lumen spaced at least 10 cm from the distal end of the catheter body.

15. The dilatation catheter of claim 14 wherein the proximal guidewire port is spaced not more than about 50 cm from the distal end of the catheter body.

16. The dilation catheter of claim 14 wherein a means is disposed within the catheter body at the proximal guidewire port which is adapted to sealingly engage a guidewire disposed therein when inflation fluid under significant pressure is introduced into the inner lumen of the catheter to inflate the inflatable member.

17. The dilation catheter of claim 13 wherein the sealing means is a tubular member with one end portion secured within the inner lumen and the other end portion thereof being tapered and adapted to sealingly engage the guidewire when inflation fluid under significant pressure is introduced into the inner lumen of the catheter to inflate the inflatable member.

18. The dilatation catheter of claim 16 wherein the tubular member is secured within the distal end of the catheter body.

19. The dilatation catheter of claim 16 wherein the tubular member is secured to the catheter body at the proximal guidewire port in fluid communication with the inner lumen of the catheter body.

20. The dilatation catheter of claim 11 wherein the sealing means is an elongated tubular element which is secured within the inner lumen by the distal extremity thereof to the distal end of the catheter body and the proximal extremity thereof extends well into the interior of the inflatable member.

21. The dilatation catheter of claim 18 wherein the elongated tubular element which forms the sealing means has an expanded section which collapses against a guidewire disposed within the inner lumen and provides sealing effects to prevent the discharge of inflation fluid.

22. The dilatation catheter of claim 11 wherein the catheter body has a single lumen extending the length thereof which is adapted to receive a guidewire and to direct inflation fluid to the inflatable member.

23. The dilatation catheter of claim 11 wherein an adapter is provided on the proximal end of the catheter shaft which has a tubular sealing means with a proximal portion secured within an inner lumen extending within the adapter and a distal portion thereof being tapered and adapted to sealingly engage the guidewire extending through the inner lumen within the adapter.

* * * * *